United States Patent
Ooue et al.

(10) Patent No.: US 11,975,541 B2
(45) Date of Patent: May 7, 2024

(54) PRINTING METHOD FOR USE IN MANUFACTURE OF DISPOSABLE WORN ARTICLES

(71) Applicant: ZUIKO CORPORATION, Osaka (JP)

(72) Inventors: Masaya Ooue, Osaka (JP); Shuji Satake, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 163 days.

(21) Appl. No.: 17/765,098

(22) PCT Filed: Sep. 25, 2020

(86) PCT No.: PCT/JP2020/036294
§ 371 (c)(1),
(2) Date: Mar. 30, 2022

(87) PCT Pub. No.: WO2021/075228
PCT Pub. Date: Apr. 22, 2021

(65) Prior Publication Data
US 2022/0339938 A1   Oct. 27, 2022

(30) Foreign Application Priority Data
Oct. 15, 2019 (JP) ................ 2019-188663

(51) Int. Cl.
*B41J 2/165* (2006.01)
*A61F 13/15* (2006.01)
*B41J 3/407* (2006.01)

(52) U.S. Cl.
CPC ........ *B41J 2/165* (2013.01); *A61F 13/15723* (2013.01); *A61F 13/15731* (2013.01);
(Continued)

(58) Field of Classification Search
CPC ...................................................... B41J 2/165
See application file for complete search history.

(56) References Cited

U.S. PATENT DOCUMENTS 5,766,389 A   6/1998   Brandon
2005/0217791 A1   10/2005   Costello
(Continued)

FOREIGN PATENT DOCUMENTS

JP   06-015815 A   1/1994
JP   2000-000266 A   1/2000
(Continued)

OTHER PUBLICATIONS

Matsumoto, Machine Translation of JP-2019142192-A, 2019 (Year: 2019).*
(Continued)

*Primary Examiner* — Scott A Richmond
(74) *Attorney, Agent, or Firm* — Renner, Otto, Boisselle & Sklar, LLP

(57) ABSTRACT

A method including: a conveying step of conveying a continuous sheet to be a component of a disposable worn article in a longitudinal direction; a printing step of repeatedly printing a predetermined pattern by spraying ink from a first group of nozzles of an inkjet print head onto a surface of the continuous sheet; and a flushing step of performing a flushing operation of spraying ink from at least a second group of nozzles of the head onto the surface of the continuous sheet.

15 Claims, 9 Drawing Sheets

(52) U.S. Cl.
CPC .. *A61F 13/15739* (2013.01); *A61F 13/15764* (2013.01); *B41J 3/407* (2013.01)

(56) References Cited

U.S. PATENT DOCUMENTS

| | | |
|---|---|---|
| 2006/0055715 A1 | 3/2006 | Nakahara |
| 2007/0057983 A1* | 3/2007 | Kawaguchi .......... B41J 2/16526 347/9 |
| 2016/0175165 A1 | 6/2016 | Schneider |
| 2020/0085642 A1* | 3/2020 | Schneider ......... A61F 13/15804 |
| 2020/0129658 A1 | 4/2020 | Maldonado |

FOREIGN PATENT DOCUMENTS

| | | | | |
|---|---|---|---|---|
| JP | 2001-315325 A | 11/2001 | | |
| JP | 2006-103279 A | 4/2006 | | |
| JP | 2007-076156 A | 3/2007 | | |
| JP | 2007-532340 A | 11/2007 | | |
| JP | 2012-187791 A | 10/2012 | | |
| JP | 2014-144049 A | 8/2014 | | |
| JP | 2016-123616 A | 7/2016 | | |
| JP | 2017-537712 A | 12/2017 | | |
| JP | 2019-025065 A | 2/2019 | | |
| JP | 2019025065 A | * 2/2019 | ............. | A61F 13/42 |
| JP | 2019-142192 A | 8/2019 | | |
| JP | 2019142192 A | * 8/2019 | | |
| JP | 2019-155599 A | 9/2019 | | |

OTHER PUBLICATIONS

Shiino, Machine Translation of JP-2019025065-A, 2019 (Year: 2019).*
International Search Report for corresponding Application No. PCT/JP2020/036294, dated Dec. 15, 2020.

* cited by examiner

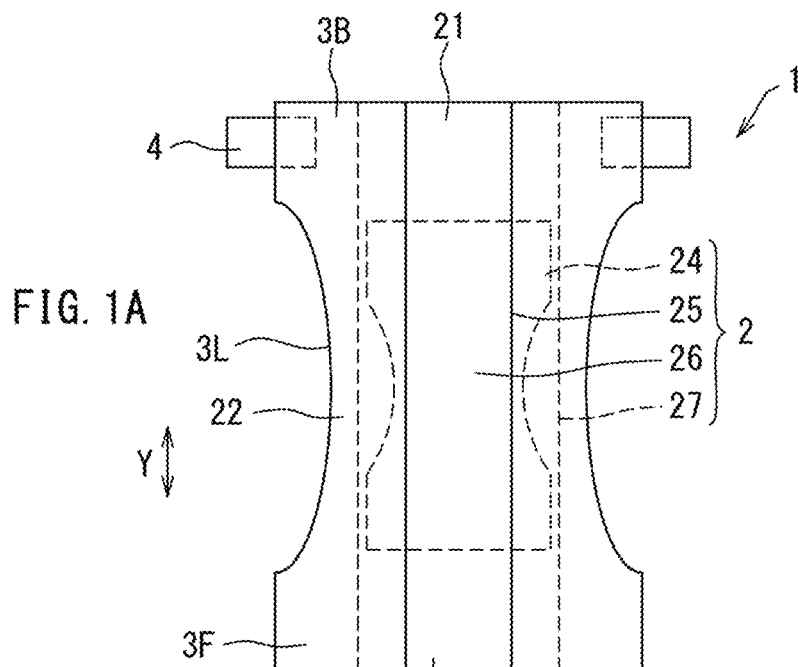
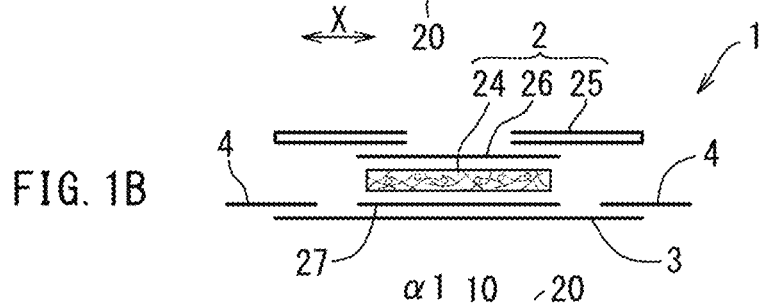
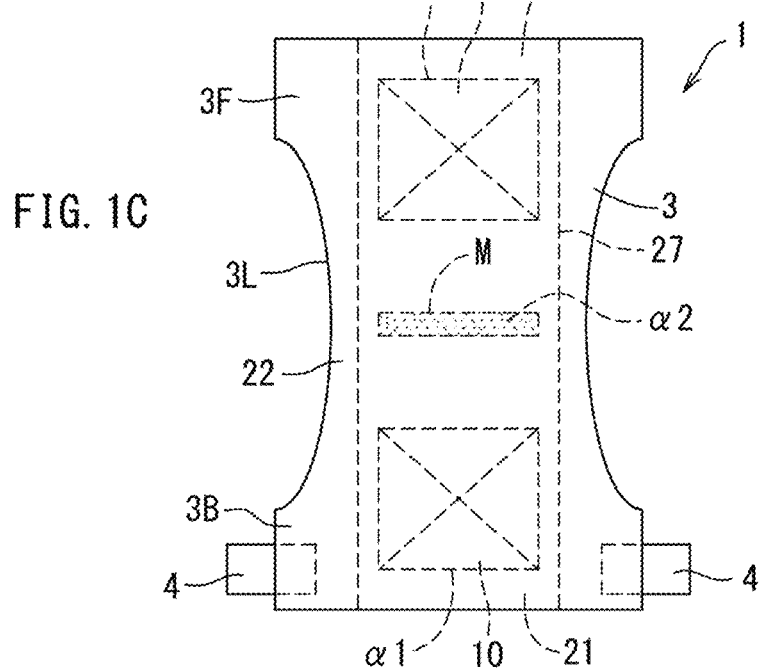

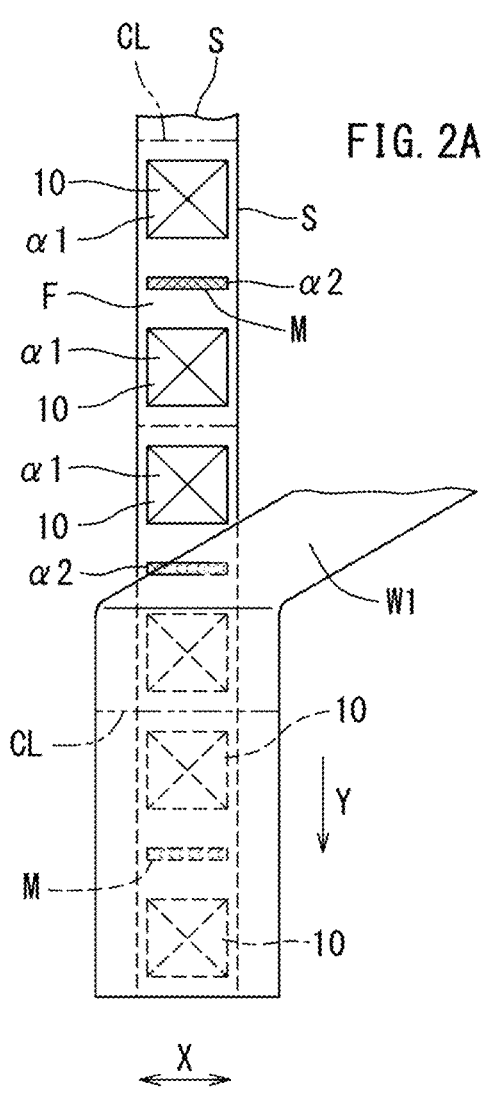
FIG. 2A
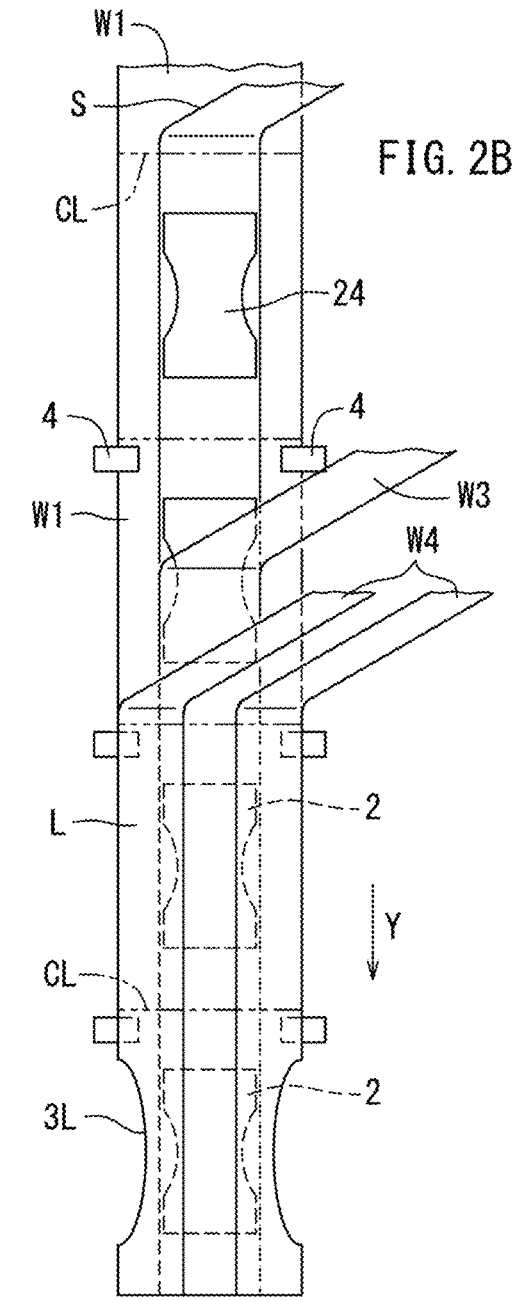
FIG. 2B
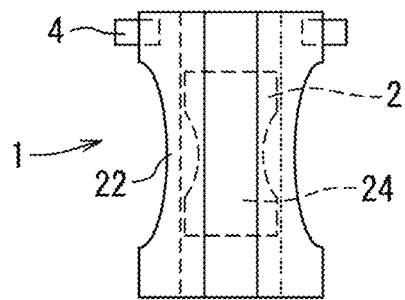

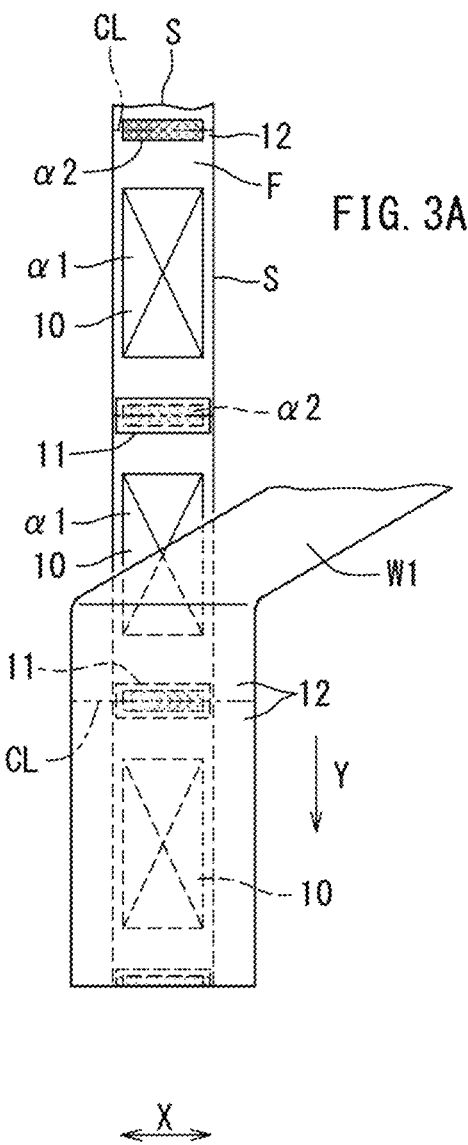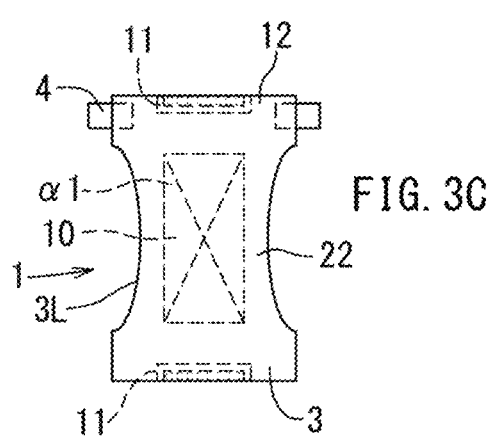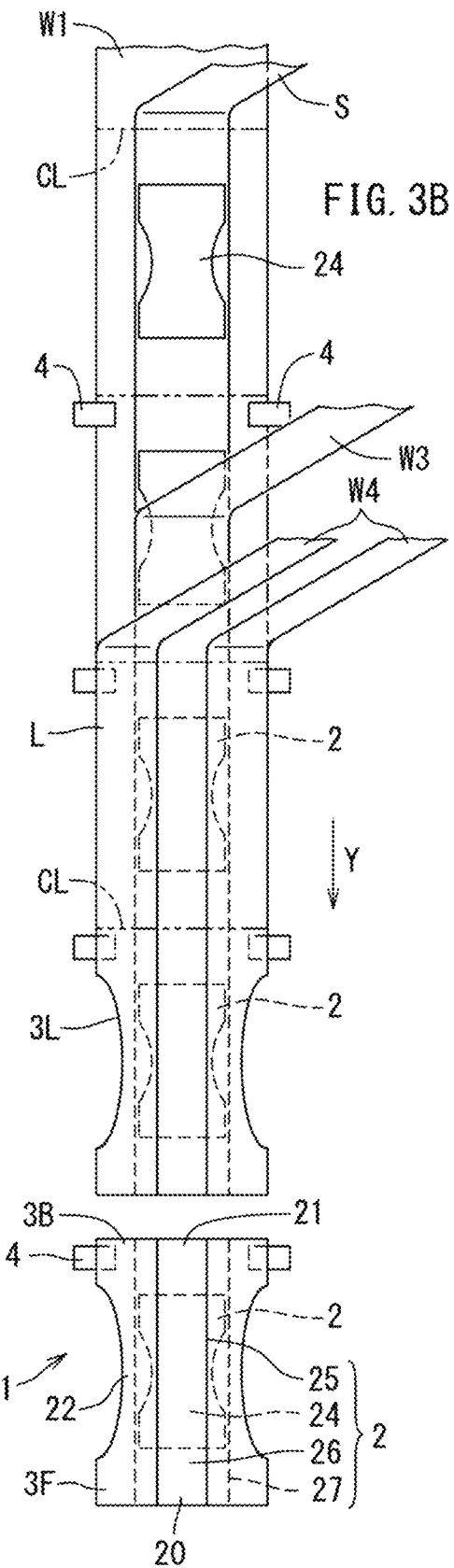

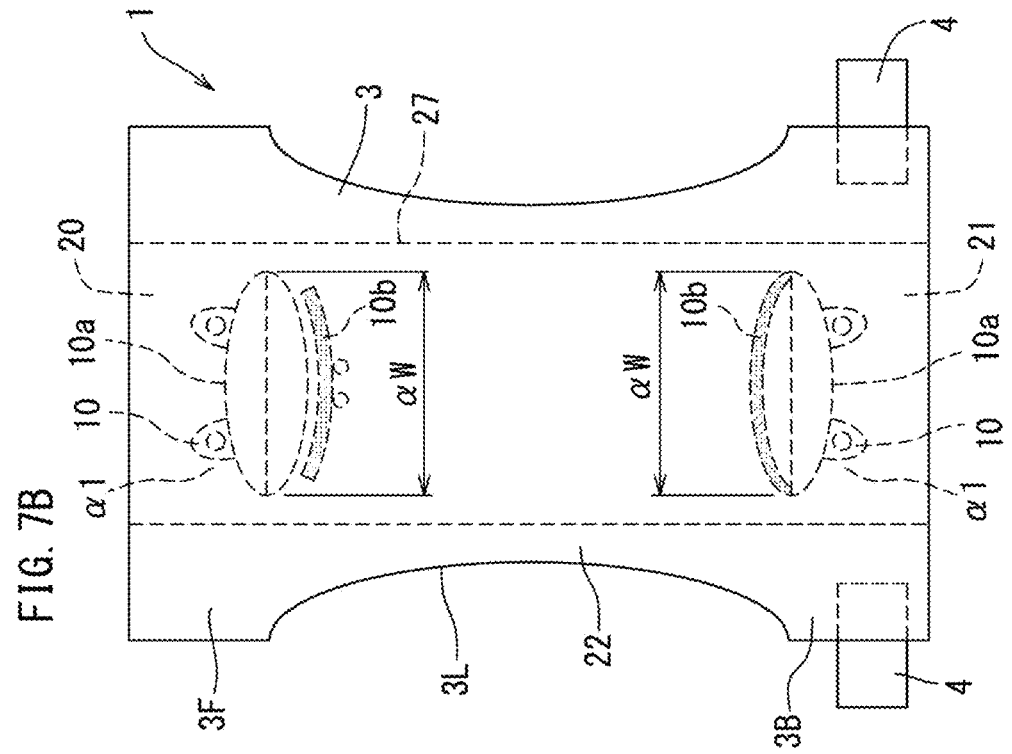
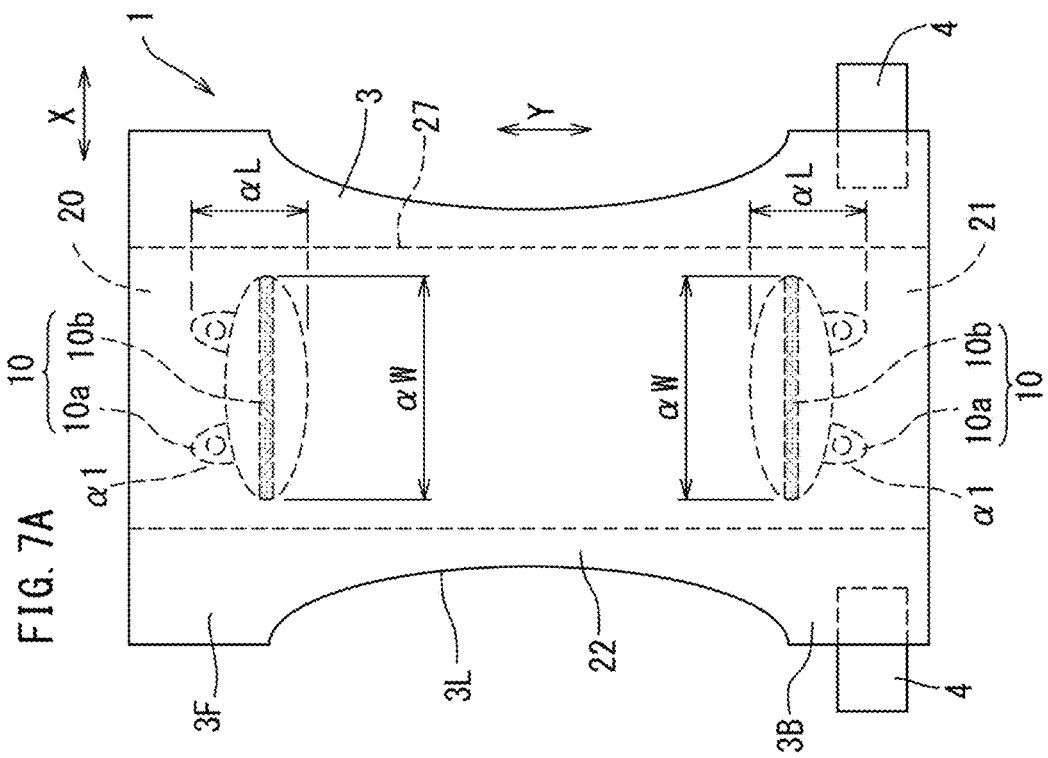

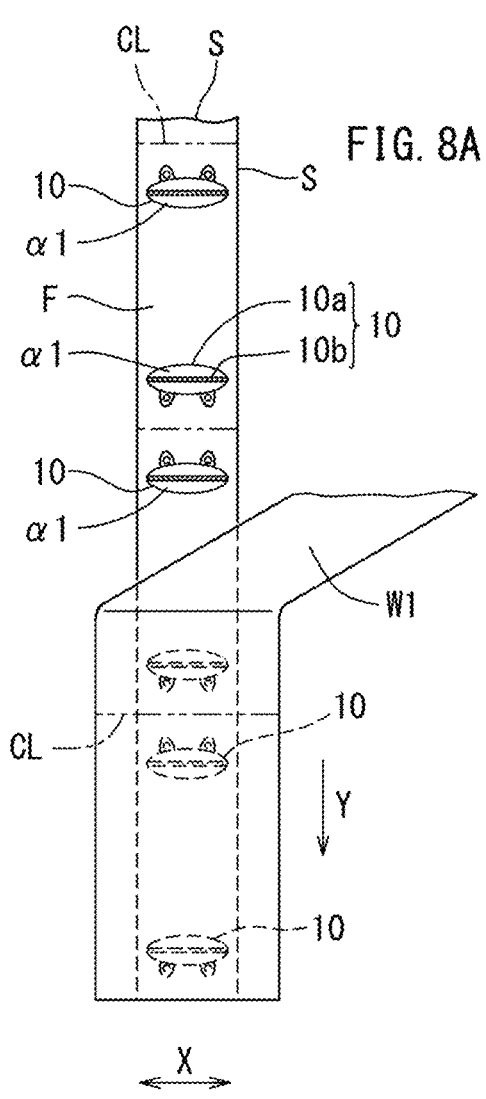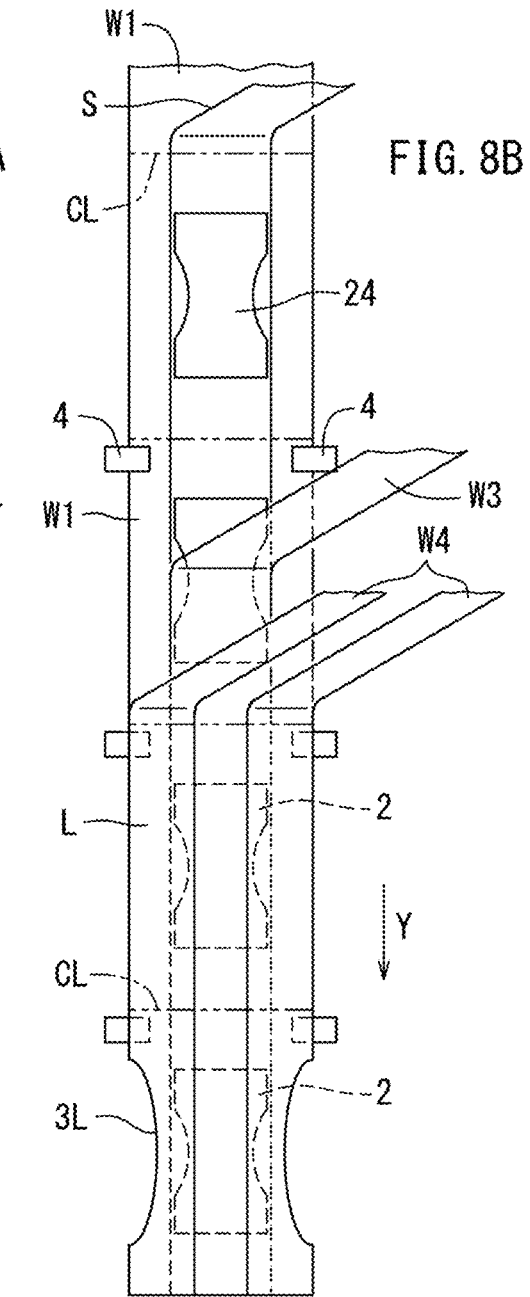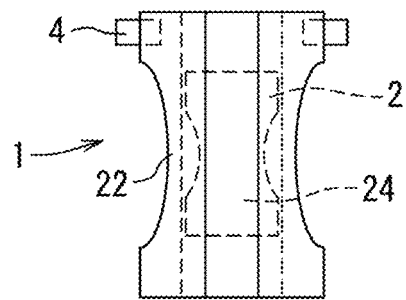

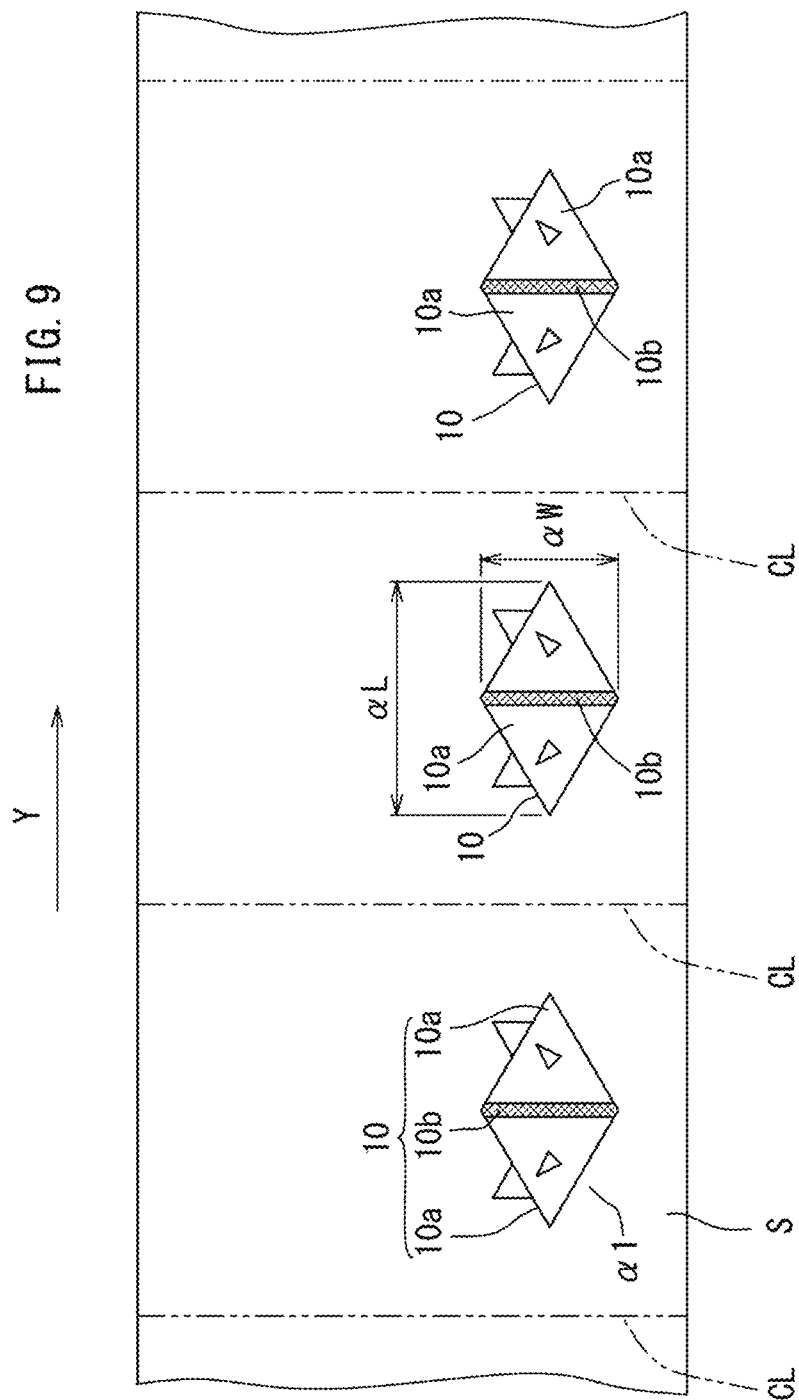

US 11,975,541 B2

PRINTING METHOD FOR USE IN MANUFACTURE OF DISPOSABLE WORN ARTICLES

TECHNICAL FIELD

The present invention relates to a printing method for use in the manufacture of disposable worn articles.

BACKGROUND ART

Some disposable diapers or pants have a pattern printed thereon as a design. As a method for printing a pattern of this type, it is a known method to repeatedly print a predetermined pattern on a continuous sheet, which is a component of the worn article, by inkjet printing during the manufacturing process of the worn article so that the pattern is repeatedly printed on each worn article (the first patent document).

CITATION LIST

Patent Document

[FIRST PATENT DOCUMENT] JP2000-266 A (front page)

SUMMARY OF INVENTION

With inkjet printing, a pattern is printed on a printing area by spraying ink from a plurality of (a large number of nozzles arranged in the width direction of the printing area. However, those nozzles that are not used to print the pattern are clogged as ink dries in the nozzles. Therefore, when the pattern is changed to another pattern, it may not be possible to realize a desired pattern as ink is not injected from the clogged nozzles.

Thus, it is an object of the present invention to prevent all nozzles from being clogged by having a flushing step in which ink is injected from nozzles that are not being used for printing a pattern in a method for manufacturing a disposable worn article, so that even when the pattern is changed to another pattern, it is possible to print a desired pattern while making it easy to process the ink that has been injected in the flushing step.

A printing method for use in manufacture of a disposable worn article of the present invention includes:

a conveying step of conveying a continuous sheet S to be a component of the disposable worn article in a longitudinal direction Y;

a printing step of repeatedly printing a predetermined pattern 10 by spraying ink from a first group of nozzles N1 of an inkjet print head H onto a surface F of the continuous sheet S; and a flushing step of performing a flushing operation of printing by spraying ink from at least a second group of nozzles N2 of the head H onto the surface F of the continuous sheet S.

According to the present invention, a flushing operation of spraying ink from at least a second group of nozzles that are different from a first group of nozzles that are used for the intended printing operation. Thus, it is possible to prevent nozzles, which are not performing the normal printing operation, from being clogged. Therefore, it is possible to realize beautiful printing even after a pattern is changed to another.

On the other hand, since the medium onto which the flushing operation is performed is the continuous sheet, there is no need to separately provide a medium onto which the flushing operation is performed, and the process will not soil the apparatus.

BRIEF DESCRIPTION OF THE DRAWINGS

FIG. 1A is a front view schematically showing an example of a worn article, which has undergone the printing method of the present invention, FIG. 1B is a cross-sectional view thereof, and FIG. 1C is a back view thereof.

FIG. 2A and FIG. 2B are a back view and a front view, respectively, schematically showing a method for manufacturing a worn article according to Embodiment 1 of the present method.

FIG. 3A and FIG. 3B are a back view and a front view, respectively, schematically showing a method for manufacturing a worn article according to Embodiment 2 thereof, and FIG. 3C is a back view of the worn article.

FIG. 7A is a back view showing a worn article according to Embodiment 5, and FIG. 7B is a back view showing a worn article according to Embodiment 6.

FIG. 8A and FIG. 8B are a back view and a front view, respectively, schematically showing a method for manufacturing a worn article according to Embodiment 5 of the present method invention.

FIG. 9 is a plan view showing a part of the manufacturing method according to Embodiment 6.

DESCRIPTION OF EMBODIMENTS

Figure 4A:
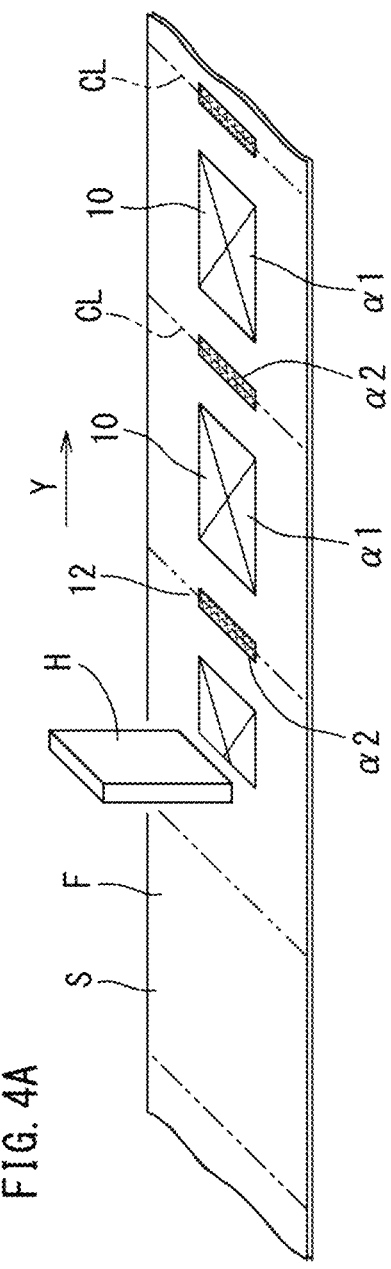
FIG. 4A and FIG. 4B are perspective views schematically showing a method for manufacturing a worn article according to Embodiment 3 of the present method as viewed from the back side and as viewed from the front side, respectively.

Preferably, the printing step includes the flushing step; and a part 10a of the pattern 10 is printed in the printing step, and a remainder 10b of the pattern 10 is printed in the flushing step.

In this case, the printing through flushing also forms the pattern. Therefore, the process is unlikely to waste ink for forming the pattern 10.

Preferably, the predetermined pattern 10 is formed in a predetermined printing area α1 through the printing in the printing step and the printing in the flushing step.

In this case, the pattern 10 is done in the predetermined printing area α1, and even if the remainder 10b of the pattern 10 is printed in the flushing step, the process is unlikely to detract from the aesthetic appearance of the articles.

Preferably, in the printing step, a part 10a of the pattern 10 is printed in an area that is more than a half of the printing area α1 in which the pattern 10 is printed; and in the flushing step, a remainder 10b of the pattern 10 is printed in an area that is smaller than the part 10a of the pattern 10.

In this case, the remainder 10b of the pattern 10 to be printed in the flushing step is small, and the process is unlikely to detract from the aesthetic appearance of the pattern 10.

Preferably, ink is sprayed from all nozzles of the head H in the flushing step.

In this case, it is possible to always prevent all nozzles from being clogged irrespective of the design (shape and color) of the pattern to be printed, and it is possible to simplify the software for nozzle selection.

In this case, the printing in the flushing step is performed over a total width, which is orthogonal to the longitudinal direction Y, of the printing area α1.

Preferably, the printing in the flushing step prints a straight portion that extends straight in a direction that is orthogonal to the longitudinal direction Y.

In this case, it is easy to set the timing for spraying ink from nozzles in the flushing step.

Preferably, the printing in the printing step is performed in a predetermined printing area α1 on a surface of the continuous sheet S; and the printing in the flushing step is performed in a flushing area α2 that is positioned differently in the longitudinal direction Y from the printing area α1 on the surface of the continuous sheet S.

Thus, since the flushing area α2 is provided separate from the printing area α1, the flushing operation will not detract from the design of the pattern 10, which is printed in the printing step.

Preferably, a reg-mark (register mark) M to be used when processing a continuous laminate L including the continuous sheet S is printed intermittently on the continuous sheet S in the flushing step.

When the reg-mark M is printed in the flushing step as described above, it will be useful in the manufacture of a disposable worn article, e.g., it can be used as a reference position for the placement of the absorbent core, for example.

Note that a reg-mark is what is officially termed a register mark, and refers to a mark that is used as various indices in processes such as printing and processing of a printed article.

Preferably, the method further includes, after the flushing step, a concealing step of concealing the flushing area α2 by arranging a concealing member on the surface F of the continuous sheet S, on which printing has been done in the flushing area α2.

In this case, since the flushing area α2 is concealed by a concealing member, portions of the print other than the intended pattern do not appear on the surface, and it will not detract from the design.

Preferably, the concealing member is an elastic strip 11 that is elongated in a width direction X of the continuous sheet S.

In this case, the elastic strip 11 serves as a part of the elastic belt of the worn article, preventing loss of materials.

Preferably, the method further includes, after the flushing step, a die-cut step of cutting out a portion of the continuous sheet S, wherein the die-cut step cuts out at least a portion of an area where printing has been done in the flushing area α2.

In this case, since at least a portion of the flushing area α2 will be punched out, portions of the print other than the intended pattern are unlikely to appear on the surface.

Preferably, the method further includes, after the flushing step, a welding step of welding together sides 3S of a front portion 20 and a back portion 21 of a continuous laminate L including the continuous sheet S for each individual article, wherein the flushing area α2 is set in areas of the continuous sheet S to be the sides, and the flushing areas α2 of the front portion 20 and the back portion 21 are welded to each other in the welding step.

In this case, the flushing area α2 is set in the so-called side seal portion, and when the disposable pants are disposed of by tearing the side seal portion, it is easy to find the position to tear.

Preferably, the method further includes a cut-off step of successively cutting off a continuous laminate L including the continuous sheet S along a virtual cut-off line CL into articles, wherein the flushing area α2 is set in a boundary portion 12 between articles that are adjacent to each other to be cut off along the cut-off line CL, and the flushing is performed in the boundary portion 12.

In this case, since the flushing area α2 is set in the boundary portion, the printed flushing area α2 can easily be made inconspicuous or cut off.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Before describing a manufacturing method according to Embodiment 1 of the present invention, an example of a structure of a worn article 1 will be described with reference to the drawings.

As shown in FIG. 1A and FIG. 1B, the worn article 1 of Embodiment 1 includes an absorbent body 2 and an external non-woven fabric 3. The absorbent body 2 includes a front portion 20, a back portion 21 and a crotch portion 22. The front portion 20 extends in the girth direction X, covering the front torso (the front portion of the torso) of the wearer. The back portion 21 extends in the girth direction X, covering the rear torso (the rear portion of the torso) of the wearer. The crotch portion 22 covers the crotch of the wearer between the front portion 20 and the back portion 21.

The crotch portion 22 is continuous with the front portion 20 and the back portion 21, and the absorbent body 2 is elongated in the vertical direction (longitudinal direction) Y perpendicular to the girth direction X.

In FIG. 1A, the present worn article is worn while the crotch portion 22 is folded in two along a virtual line that is parallel to the girth direction X. Thus, the end portions of the front portion 20 and the back portion 21 in the girth direction X, i.e., the sides thereof, overlap with each other.

As shown in FIG. 1B, an absorbent core 24 is provided on the absorbent body 2. The absorbent core 24 absorbs body fluids. The absorbent core 24 is sandwiched between a top sheet 26 and a back sheet 27. The sheets 26, 27 and the absorbent core 24 are laminated on each other.

In FIG. 1B, the top sheet 26 is made of a thin, liquid-permeable non-woven fabric and covers the skin-contact surface of the absorbent core 24. A cuff 25 may be provided on the top sheet 26.

In the present invention, the "skin-contact surface" refers to an inner surface that directly or indirectly contacts the skin of the wearer when the diaper is worn, and directly or indirectly opposes to the skin of the wearer.

The back sheet 27 covers the non-skin-contact surface of the absorbent core 24 and is made of a liquid-impermeable resin sheet. An air-permeable exterior non-woven fabric 3 is bonded and laminated to the non-skin-contact surface of the back sheet 27.

In the present invention, the "non-skin-contact surface" refers to an outer surface, opposite to the skin-contact surface, that does not contact the skin of the wearer when the diaper is worn, and does not oppose the skin of the wearer.

The front and rear girth portions 3F, 3B may be provided with elastic members for the waist and hips. The external non-woven fabric 3 may include elastic members sandwiched between two non-woven fabrics 3. The elastic members are for fitting the girth portions 3F, 3B to the wearer. For example, the elastic members may use a thread-shaped or strip-shaped material including a plurality of rubber threads or rubber strips or a thermoplastic resin (hot melt) or a foamed urethane.

The absorbent body 2 may have around-leg portions (leg holes) 3L that are narrowed in conformity to the legs of the wearer. Other elastic members made of rubber threads, or the like, for example, may be provided along the around-leg portions 3L and in portions of the girth portions 3F, 3B that are connected to the around-leg portions so as to conform to the legs of the wearer. Note that the around-leg portions 3L become leg holes 3L when worn.

When the worn article is a diaper, a tape material 4 coated with a fastening agent may be secured to the girth portion 3B. Note that instead of the tape material 4, a male touch fastener (not shown) may be secured to the rear girth portion 3B as a fastening member, and a female touch fastener may be secured to the non-skin-contact surface of the front girth portion 3F. Note that if the worn article is of the pants type, as will be described below, the end portions of the front flap and the rear flap in the girth direction X may be welded together.

FIG. 1C shows a back view of the diaper.

In this example, a printing area α1 is provided on at least one of the front portion 20 and the back portion 21. A pattern 10 such as the face of an animal is printed in the printing area α1.

In this example, a flushing area α2 is provided in the crotch portion 22. The flushing area α2 has a strip shape elongated in the width direction, and a gray or muddy color reg-mark M is printed, for example. Note that the reg-mark M may be a geometric pattern, or the like, that has an elongated strip shape.

In this example, the pattern 10 and the reg-mark M are printed on the back sheet 27 of FIG. 1B. Since the back sheet 27 is covered by the exterior non-woven fabric 3, the pattern 10 and the reg-mark M can be seen through the exterior non-woven fabric 3.

Next, a method for manufacturing the present worn article will be described with reference to FIG. 2A and FIG. 2B. This example shows the case of a so-called longitudinal flow.

As shown in FIG. 2A, a conveying step is executed by conveying a continuous sheet S to be the liquid-impermeable back sheet 27 (FIG. 1B) whose longitudinal direction Y is set in the conveying direction.

Figure 6A:
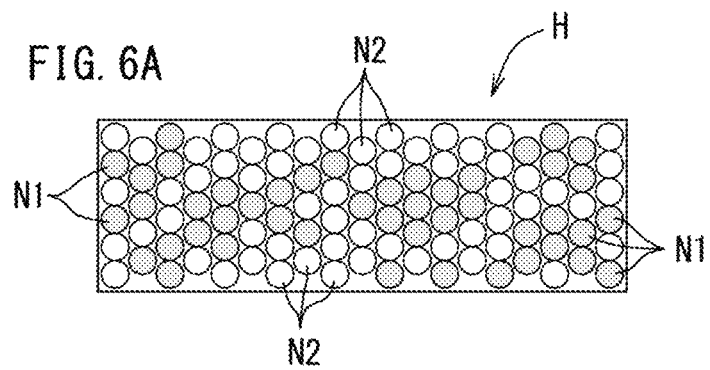
FIG. 6A, FIG. 6B and FIG. 6C are schematic conceptual diagrams each showing a group of nozzles of a print head.

During this conveying step, a printing step is executed in which ink is sprayed from a first group of nozzles N1 of an inkjet print head H of FIG. 6A onto the predetermined printing area α1 on a surface F of the continuous sheet S, thereby repeatedly printing the predetermined pattern 10 of FIG. 2A. The first group of nozzles N1 in FIG. 6A are colored in gray. On the other hand, the second group of nozzles N2, which are different from the first group of nozzles N1 in FIG. 6A, are not colored.

Figure 6B:
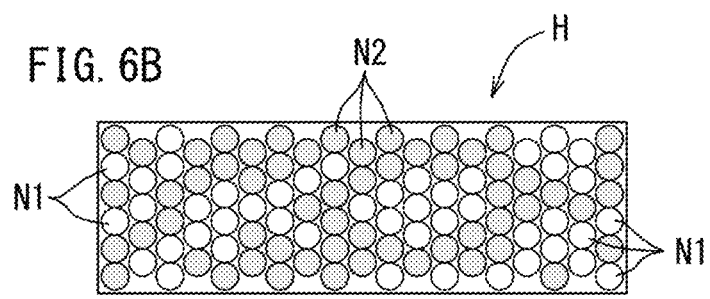

During the conveying step, a flushing step is executed in which printing is performed through a flushing operation of injecting ink from the second group of nozzles N2 of the head H of FIG. 6B onto the flushing area α2, which is positioned differently in the longitudinal direction Y from the printing area α1, on the surface F of the continuous sheet S of FIG. 2A. The second group of nozzles N2 in FIG. 6B are colored in gray. On the other hand, the first group of nozzles N1 are not colored in FIG. 6B.

Now, the relationship between the first group of nozzles N1 and the second group of nozzles N2 will be explained.

In this example of FIG. 6A and FIG. 6B, all the nozzles of the head H belong to either the first group of nozzles N1 or the second group of nozzles N2. Nozzles belonging to the first group of nozzles N1 do not belong to the second group of nozzles N2, while nozzles belonging to the second group of nozzles N2 do not belong to the first group of nozzles N1.

In this example, ink is injected from all nozzles in either the printing step or the flushing step, and it is possible to prevent nozzles from being clogged.

Figure 6C:
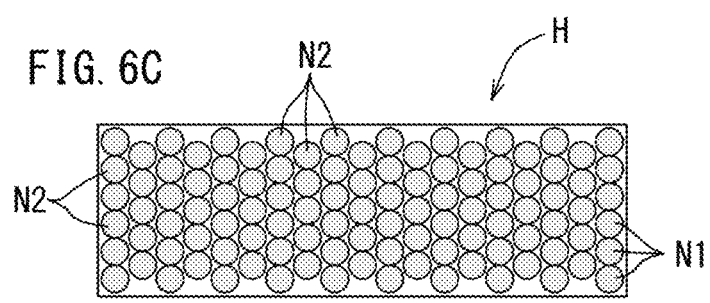

In another example shown in FIG. 6C, nozzles colored in gray may all belong to the second group of nozzles N2. In this example, all nozzles of the first group of nozzles N1 of FIG. 6A also belong to the second group of nozzles N2 of FIG. 6C.

In the examples of FIG. 6A and FIG. 6C, ink is injected from all nozzles in the flushing step, and it is possible to prevent nozzles from being clogged.

Figure 6D:
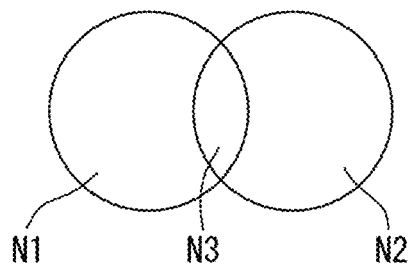
FIG. 6D shows, in set theory, the concept of a group of nozzles.

In the flushing step, ink may be injected from nozzles other than those that belong to the first group of nozzles N1 of FIG. 6A. For example, as explained in set theory, a common part N3 may exist partially between the set of the first group of nozzles N1 and the set of the second group of nozzles N2 of FIG. 6D.

This is because it is possible to prevent nozzles from being clogged also in this case.

As shown in FIG. 2A, since the flushing areas α2 are present intermittently on the continuous sheet S, the nozzles to spray may be dispersed over flushing steps so that nozzles that spray over a plurality of flushing steps may together constitute the second group of nozzles N2. For example, ink may be injected from some nozzles of the second group of nozzles N2 in the first flushing step and ink may be injected from the remaining nozzles of the second group of nozzles N2 in the second flushing step.

In this example, as shown in FIG. 2A and FIG. 1C, the printing area α1 is provided in both of the front portion 20 and the back portion 21. On the other hand, the flushing area α2 may be set in the crotch portion 22, and the reg-mark M of a strip shape that is elongated in the width direction X of the continuous sheet S may be printed. This reg-mark M is printed intermittently at a certain pitch on the continuous sheet S of FIG. 2A, and is used as a portion to be detected when processing the continuous laminate L of FIG. 2B including the continuous sheet S.

After the printing and flushing step of FIG. 2A, the continuous sheet S is laminated onto a non-woven fabric web W1. As a result, the pattern 10 can be seen through the non-woven fabric web W1.

An adhesive is applied to the continuous sheet S or the non-woven fabric web W1. Thus, the continuous sheet S is attached to the non-woven fabric web W1 to produce a laminated intermediate product.

After the placement of the continuous sheet S of FIG. 2B, the absorbent core 24 may be arranged on each continuous sheet S and the absorbent core 24 may be attached to the continuous sheet S.

Thereafter, a pair of tape materials 4 of FIG. 2B are attached to the non-woven fabric web W1, and a liquid-permeable continuous web W3 to be the top sheet 26 is further laminated so as to cover the absorbent core 24 and the continuous sheet S.

Then, a pair of cuff continuous webs W4 to be the cuffs 25 (FIG. 1B) are laminated to produce a continuous laminate (intermediate product) L. After the lamination, a portion of the non-woven fabric web W1 may be partially notched to form a portion to be the leg hole 3L.

Thereafter, in order to obtain individual worn articles 1 from the continuous laminate L of FIG. 2B, the continuous laminate L is cut off along a virtual cut-off line CL that extends in the width direction X orthogonal to the conveying direction Y. Note that the continuous laminate L is cut off between the absorbent bodies 2, 2 adjacent to each other. Thus, the worn article 1 shown in FIG. 1A to FIG. 1C is obtained.

Note that in this example, the width direction X of the continuous sheet S is the girth direction X of the worn article, and the conveying direction Y of the continuous laminate L is the longitudinal direction Y of the worn article.

FIG. 3A to FIG. 3C show Embodiment 2 also for the longitudinal flow.

In this example, the flushing area $\alpha 2$ is set in a boundary portion 12 between articles that are adjacent to each other, and the flushing is performed in the boundary portion 12. The boundary portion 12 may include the cut-off line CL. The printing area $\alpha 1$ may be set across the entire area from the front portion 20 to the back portion 21.

In this example, after the flushing step of FIG. 3A, a concealing step is further performed in which an elastic strip (an example of the concealing member) 11 elongated in the width direction X of the continuous sheet S is arranged on the surface F of the continuous sheet S, on which printing has been done in the flushing area $\alpha 2$, so as to cover the flushing area $\alpha 2$.

The elastic strip 11 arranged in the flushing area $\alpha 2$ is formed of a foamed resin, for example, and stretches/shrinks in the girth direction X in the back portion 21 and the front portion 20 of the worn article 1 of FIG. 3B to fit the crotch portion 22 to the waist of the wearer.

Figure 4B:
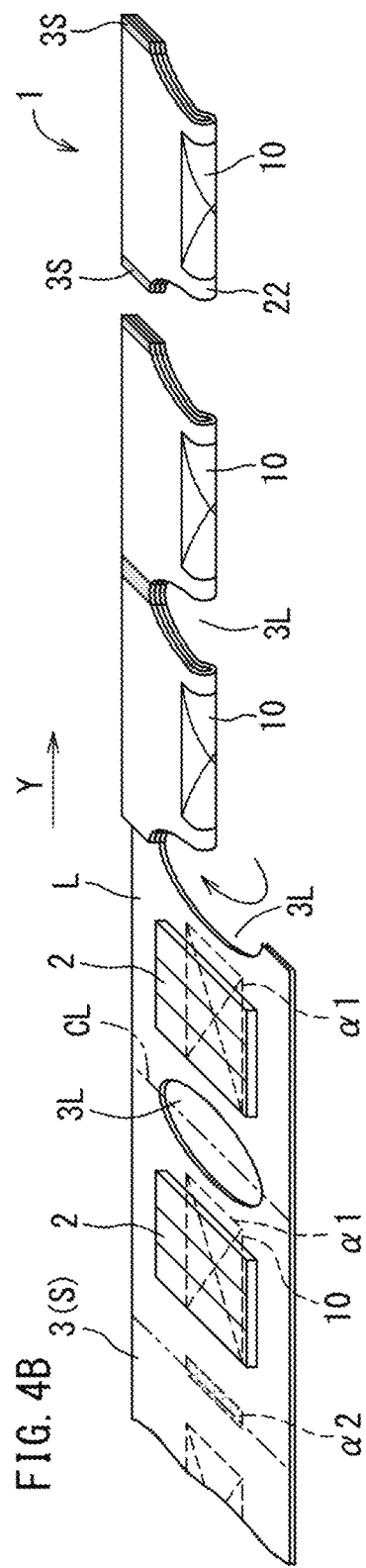
Figure 5A:
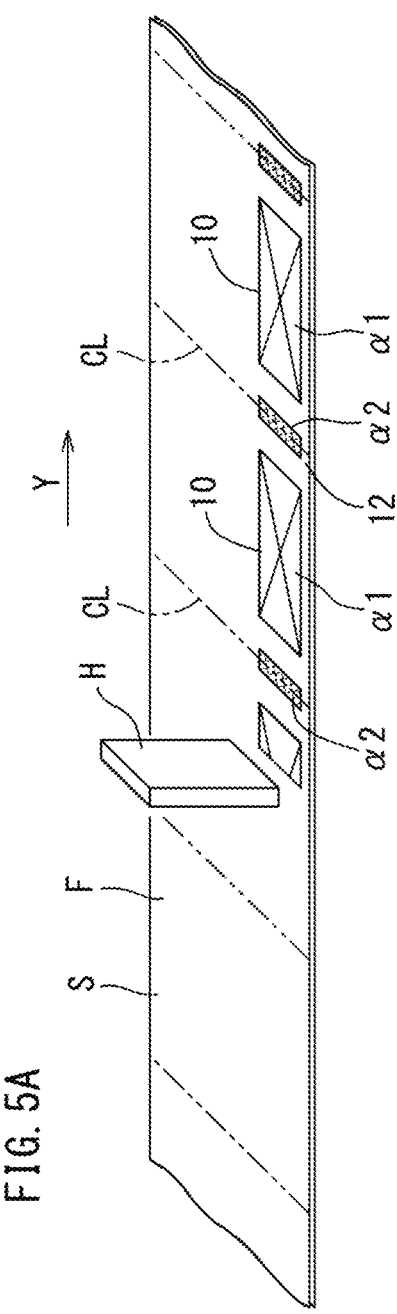
FIG. 5A and FIG. 5B are perspective views schematically showing a method for manufacturing a worn article according to Embodiment 4 thereof as viewed from the back side and as viewed from the front side, respectively.
Figure 5B:
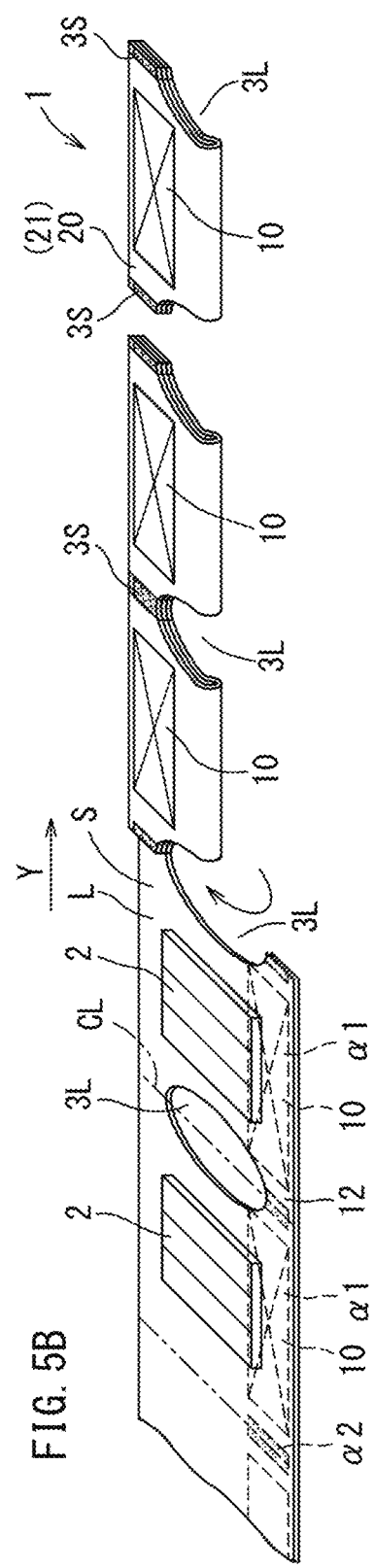

FIG. 4A to FIG. 4B and FIG. 5A to FIG. 5B show the case where pairs of pants are produced in a so-called lateral flow. FIG. 4A to FIG. 4B show Embodiment 3, and FIG. 5A to FIG. 5B show Embodiment 4.

Note that in such an example of the lateral flow, the conveying direction Y of the continuous sheet S is the girth direction of the worn article.

As shown in FIG. 4B and FIG. 5B, the pants have the sides 3S of the front portion and the back portion welded to each other. In the example of FIG. 4B, the pattern 10 is printed on the crotch portion 22, and in the example of FIG. 5B, the pattern 10 is printed on at least one of the front portion 20 and the back portion 21.

In these examples, a pattern is printed intermittently along the continuous sheet S of FIG. 4A, which is to be the external non-woven fabric 3 of FIG. 4B, so that a pattern is printed on each individual article. The exterior non-woven fabric 3 of this example may include a pair of webs and elastic members that stretch/shrink in the girth direction sandwiched therebetween.

On the other hand, the absorbent body 2 of FIG. 4B includes an absorbent core sandwiched between the back sheet and the top sheet, and may have a cuff on the skin-contact surface side.

Next, a method for manufacturing the pants of FIG. 4A to FIG. 4B will be described.

As shown in FIG. 4A, the printing step is executed on the continuous sheet S by spraying ink from the head H in the printing area $\alpha 1$ for each individual article. On the other hand, in this example, in the flushing area $\alpha 2$, the flushing step is executed in the boundary portion 12 including the virtual cut-off line CL by spraying ink from the head H. These printing operations may be performed on the non-skin-contact surface side of the continuous sheet S or on the skin-contact surface side thereof. This is because it can be seen through even on the skin-contact surface side.

The printing operation, etc., described above are performed on the external non-woven fabric 3 (FIG. 4B) as the continuous sheet S. Thereafter, as shown in FIG. 4B, the absorbent bodies 2 are arranged one after another on the inner surface side (skin-contact surface) of the external non-woven fabric 3.

In this example, after the printing step and the flushing step of FIG. 4A, a die-cut step of cutting out a part of the continuous sheet S of FIG. 4B is provided. The area that is printed in the flushing area $\alpha 2$ is cut out in the die-cut step described above, and becomes a part of the leg hole 3L. Note that there is no need to cut out all of the flushing area $\alpha 2$, but a part of the flushing area $\alpha 2$ may remain as a part of the pants.

Then, the continuous laminate L is folded in two so that the skin-contact surfaces of the front portion and the back portion oppose each other. After this folding, a welding step of welding together the sides 3S of the front portion and the back portion of the continuous laminate L including the continuous sheet S for each individual article is executed.

After this welding, the continuous laminate L is cut off into individual worn articles 1.

Next, a method for manufacturing the pants of FIG. 5A to FIG. 5B will be described.

As shown in FIG. 5A, a printing operation is performed by spraying ink from the head H in the area of the continuous sheet S to be the front portion or the back portion, i.e., the printing area $\alpha 1$. On the other hand, in the flushing area $\alpha 2$ between a printing area $\alpha 1$ and a printing area $\alpha 1$, that is, in the boundary portion 12 including the cut-off line CL, the flushing step is executed in which ink is sprayed from the head H.

After the absorbent body 2 is arranged in the same manner as in Embodiment 3, the die-cut step is executed to form the leg holes 3L. During this die-cut step, a portion of the flushing area $\alpha 2$ is cut out.

After the die-cut step described above, the welding step is executed.

The remainders of the flushing area $\alpha 2$ are set in the areas of the continuous sheet S that are to be the sides, and the remainders of the flushing area $\alpha 2$ in the front portion and the back portion are welded to each other in the welding step.

After welding, the continuous laminate L is cut off into individual worn articles 1.

Note that in the flushing step, the second group of nozzles N2 of FIG. 6B may spray at the same time or each nozzle of the second group of nozzles N2 may spray with different timing.

The flushing process may be performed for each worn article or may be performed once for a plurality of worn articles.

Next, the diaper of FIG. 7A of Embodiment 5 and a method for manufacturing the same will be described. Before describing the manufacturing method, the diaper of FIG. 7A will be described.

In FIG. 7A, the pattern 10 is printed in the printing area α1, and is composed of a main portion (an example of the part) 10a denoted by a broken line and a secondary portion (an example of the remainder) 10b denoted by a grid pattern. The main portion 10a is the main portion of the pattern 10, while the secondary portion 10b is the remainder of the pattern 10.

In FIG. 7A and FIG. 7B, the main portion 10a is printed in the printing step, and the secondary portion 10b is printed in the flushing step. Therefore, each pattern 10 is formed (printed) by spraying ink from all nozzles.

In the printing step, the main portion 10a of the pattern 10 is printed in an area that is more than a half of the printing area α1 in which the pattern 10 is printed. On the other hand, in the flushing step, the secondary portion 10b of the pattern 10 is printed in an area that is smaller than the main portion 10a of the pattern 10.

in the example of FIG. 7A, the main portion 10a is printed over the total width αW, which is orthogonal to the longitudinal direction Y, of the printing area α1, and over the total length αL. The secondary portion 10b is also printed over the total width αW of the printing area α1.

In the example of FIG. 7A, the secondary portion 10b is formed by a straight portion that extends straight in the width direction X, which is orthogonal to the longitudinal direction Y. Here, although the secondary portion 10b is shown as a thick strip shape for the secondary portion 10b is depicted with a grid pattern, the secondary portion 10b may be printed as a thin line because it is used as the secondary portion 10b of the pattern 10.

As shown in FIG. 7A, a plurality of patterns 10, or one pattern 10, may be provided on one worn article. One pattern 10 or a plurality of patterns 10 may be printed in each of the front portion 20 and the back portion 21 of the diaper.

Next, a method for manufacturing the diaper of FIG. 7A will be described with reference to FIG. 8A and FIG. 8B. In this example, the manufacturing process other than the printing of the pattern 10 is similar to the example of FIG. 2A and FIG. 2B described above, and the description below will focus on the printing step and the flushing step.

During the conveying step of conveying the continuous sheet S of FIG. 8A, the main portion 10a is printed by spraying ink from the first group of nozzles N1 (FIG. 6A) of the print head onto the predetermined printing area α1 on the surface of the continuous sheet S, and the secondary portion 10b is printed by spraying ink from all nozzles including the second group of nozzles N2 (FIG. 6B).

In FIG. 8A, the printing step includes the flushing step, and the main portion 10a, which is a part of the pattern 10 of FIG. 7A, is printed in the printing step, and the secondary portion 10b, which is the remainder of the pattern 10, is printed in the flushing step. Thus, the predetermined pattern 10 is formed in the predetermined printing area α1 through the printing in the printing step and the printing in the flushing step.

In FIG. 7A, the printing in the flushing step is performed over the total width αW, which is orthogonal to the longitudinal direction Y, of the printing area α1. In this example, ink is sprayed in the flushing step from all nozzles generally at the same time, and the printing in the flushing step forms, as the secondary portion 10b, a straight portion that extends straight in the width direction X, which is orthogonal to the longitudinal direction Y.

Note that in the example of FIG. 7A to FIG. 8B, the width direction X of the continuous sheet is the girth direction X of the worn article, and the conveying direction Y of the continuous laminate L is the longitudinal direction Y of the worn article.

FIG. 7B shows a diaper of Embodiment 6.

As shown in FIG. 7B, the pattern 10 may differ between the front portion 20 and the back portion 21. The secondary portion 10b printed in the flushing step may have a curved shape rather than a straight shape.

Moreover, the secondary portion 10b may have a width smaller than the total width αW of the printing area α1, as in the pattern 10 of the front portion 20 of FIG. 7B. In such a case, those nozzles that do not spray ink in the flushing step spray ink when printing the main portion 10a.

FIG. 9 shows a printing step according to Embodiment 6.

This example shows a case where pants are produced in the lateral flow of the example of FIG. 4A. In this example of FIG. 9, the printing step of printing the pattern 10 and the flushing step are similar to those of the example of FIG. 8 described above.

For example, in FIG. 9, a right portion of the main portion 10a is first printed. in the first printing step, the secondary portion 10b is then printed in the flushing step, and the left portion of the main portion 10a is printed again in the second printing step.

While preferred embodiments have been described above with reference to the drawings, obvious variations and modifications will readily occur to those skilled in the art upon reading the present specification.

For example, the printing may be done on a continuous absorbent body of H-shaped diapers or pants.

The web to be the top sheet may be laminated intermittently.

Thus, such variations and modifications shall fall within the scope of the present invention as defined by the appended claims.

INDUSTRIAL APPLICABILITY

The present invention is applicable to the manufacture of diaper-type and pants-type disposable worn articles, etc.

REFERENCE SIGNS LIST

1: Disposable worn article
10: Pattern, 10a: Main portion (an example of the part), 10b: Secondary portion (an example of the remainder), 11 Strip, 12: Boundary portion
2: Absorbent body, 20: Front portion, 21: Back portion, 22: Crotch portion
24: Absorbent core, 25: Cuff, 26: Top sheet, 27: Back sheet
3: External non-woven fabric, 3F, 3B: Girth portion, 3L: Leg hole,
3S: Side
4: Tape material (fastening member)

CL: Cut-off line, F: Surface, H: Head
L: Continuous laminate, M: Reg-mark
Ni: First group of nozzles, N2: Second group of nozzles
α1: Printing area, α2: Flushing area
X: Width direction, Y: Longitudinal direction
W1: Non-woven fabric web, W3: Permeable continuous web, W4: Cuff continuous web

The invention claimed is:

1. A printing method for use in manufacture of a disposable worn article, comprising:
   a conveying step of conveying a continuous sheet to be a component of the disposable worn article in a longitudinal direction;
   a printing step of repeatedly printing a predetermined pattern by spraying ink from a first group of nozzles of an inkjet print head onto a surface of the continuous sheet; and
   a flushing step of performing a flushing operation of printing by spraying ink from at least a second group of nozzles of the head onto the surface of the continuous sheet,
   the printing in the printing step is performed in a predetermined printing area on a surface of the continuous sheet,
   the printing in the flushing step is performed in a flushing area that is positioned differently in the longitudenal direction from the printing area on the surface of the continuous sheet, and
   after the flushing step a concealing step of concealing the flushing area by arranging a concealing member on the surface of the continuous sheet on which printing has been done in the flushing area.

2. The printing method according to claim 1, wherein ink is sprayed from all nozzles of the head in the flushing step.

3. The printing method according to claim 2, wherein the printing in the flushing step is performed over a total width, which is orthogonal to the longitudinal direction, of the printing area.

4. The printing method according to claim 3, wherein the printing in the flushing step prints a straight portion that extends straight in a direction that is orthogonal to the longitudinal direction.

5. The printing method according to claim 1, wherein a reg-mark to be used when processing a continuous laminate including the continuous sheet is printed intermittently on the continuous sheet by a printing method as set forth in the flushing step.

6. The printing method according to claim 1, wherein the concealing member is an elastic strip that is elongated in a width direction of the continuous sheet.

7. The printing method according to claim 1, further comprising, after the flushing step, a die-cut step of cutting out a portion of the continuous sheet,
   wherein the die-cut step cuts out at least a portion of an area where printing has been done in the flushing area.

8. The printing method according to claim 1, further comprising a cut-off step of successively cutting off a continuous laminate including the continuous sheet along a virtual cut-off line into articles,
   wherein the flushing area is set in a boundary portion between articles that are adjacent to each other to be cut off along the cut-off line, and the flushing is performed in the boundary portion.

9. A printing method for use in manufacture of a disposable worn article, comprising:
   a conveying step of conveying a continuous sheet to be a component of the disposable worn article in a longitudinal direction;
   a printing step of repeatedly printing a predetermined pattern by spraying ink from a first group of nozzles of an inkjet print head onto a surface of the continuous sheet; and
   a flushing step of performing a flushing operation of printing by spraying ink from at least a second group of nozzles of the head onto the surface of the continuous sheet,
   the printing in the printing step is performed in a predetermined printing area on a surface of the continuous sheet,
   the printing in the flushing step is performed in a flushing area that is positioned differently in the longitudinal direction from the printing area on the surface of the continuous sheet,
   after the flushing step, a welding step of welding together sides of a front portion and a back portion of a continuous laminate including the continuous sheet for each individual article, and
   wherein the flushing area is set in areas of the continuous sheet to be the sides, and the flushing areas of the front portion and the back portion are welded to each other in the welding step.

10. The printing method according to claim 9, wherein ink is sprayed from all nozzles of the head in the flushing step.

11. The printing method according to claim 10, wherein the printing in the flushing step is performed over a total width, which is orthogonal to the longitudinal direction, of the printing area.

12. The printing method according to claim 11, wherein the printing in the flushing step prints a straight portion that extends straight in a direction that is orthogonal to the longitudinal direction.

13. The printing method according to claim 9, wherein a reg-mark to be used when processing a continuous laminate including the continuous sheet is printed intermittently on the continuous sheet by a printing method as set forth in the flushing step.

14. The printing method according to claim 9, further comprising, after the flushing step, a die-cut step of cutting out a portion of the continuous sheet,
   wherein the die-cut step cuts out at least a portion of an area where printing has been done in the flushing area.

15. The printing method according to claim 9, further comprising a cut-off step of successively cutting off a continuous laminate including the continuous sheet along a virtual cut-off line into articles,
   wherein the flushing area is set in a boundary portion between articles that are adjacent to each other to be cut off along the cut-off line, and the flushing is performed in the boundary portion.

* * * * *